United States Patent [19]
Bertola et al.

[11] Patent Number: 6,040,460
[45] Date of Patent: Mar. 21, 2000

[54] HIGH PRODUCTIVITY PROCESS TO PRODUCE MALEIC ANHYDRIDE FROM N-BUTANE

[75] Inventors: Aldo Bertola, Milan; Salvatore Cassarino, Rome, both of Italy

[73] Assignee: Pantochim S.A., Feluy, Belgium

[21] Appl. No.: 09/337,542

[22] Filed: Jun. 22, 1999

[30] Foreign Application Priority Data

Jun. 23, 1998 [BE] Belgium ................................ 09800475

[51] Int. Cl.⁷ ................................................ C07D 307/36
[52] U.S. Cl. ............................................................ 549/262
[58] Field of Search ............................................. 549/262

[56] References Cited

U.S. PATENT DOCUMENTS

| | | |
|---|---|---|
| 3,899,516 | 8/1975 | Dickason . |
| 3,904,652 | 9/1975 | Frank . |
| 4,222,945 | 9/1980 | Higgins et al. . |
| 4,231,943 | 11/1980 | Paradis et al. . |
| 4,342,699 | 8/1982 | Palmer et al. . |
| 5,011,945 | 4/1991 | Taheri . |
| 5,069,687 | 12/1991 | Bertola et al. . |
| 5,126,463 | 6/1992 | Ramachandran et al. . |
| 5,688,970 | 11/1997 | Ruggieri et al. . |

OTHER PUBLICATIONS

T.C. Bissot et al., "Oxidation of Butane to Maleic Anhydride", I & EC Product Research and Development, vol. 2, No. 2, pp. 57–60, 1963.

*Primary Examiner*—Johann Richter
*Assistant Examiner*—Joseph Murray
*Attorney, Agent, or Firm*—Stevens, Davis, Miller & Mosher, L.L.P.

[57] ABSTRACT

In producing maleic anhydride by catalytic oxidation of n-butane in vapor phase using oxygen or enriched air as oxidation medium, the reaction mixture consists of butane, oxygen and a recycling exhaust gas recovered from the absorption stage by a solvent of the maleic anhydride produced in the reaction. In the instant process the carbon monoxide and the carbon dioxide concentration in the reactor mixture are held to on optimum level by performing the reaction on a suitable V.P.O. catalyst, and by feeding to the recycling gases, in addition to butane and oxygen, a carbon dioxide rich gas stream.

The carbon dioxide rich gas stream can be produced either by selective absorption and desorption of carbon dioxide from a gaseous stream purged from the recycling exhaust gases or by selective separation on membranes of a carbon dioxide rich stream from the purge gas stream, or by selective catalytic oxidation of carbon monoxide to carbon dioxide of a gaseous stream purged from the recycling exhaust gases. As an alternative, a carbon dioxide rich gas from an external source can be used. The yield of the process is further improved by recovering a large percentage of the butane contained in the purge gas by a special absorption technique. Compared with the conventional technology, the process offers superior yield, higher productivity, reduced energy of compression, safer operation, reduced environmental impact due to a remarkable reduction in carbon dioxide release.

32 Claims, 4 Drawing Sheets

6,040,460

HIGH PRODUCTIVITY PROCESS TO PRODUCE MALEIC ANHYDRIDE FROM N-BUTANE

This application claims priority under 35 USC §119 from Belgian patent application 09800475 filed Jun. 23, 1998, incorporated herein by reference in its entirety.

FIELD OF INVENTION

The present invention relates to a process for the production of maleic anhydride by oxidation of n-butane with molecular oxygen or a molecular oxygen containing gas in the vapor phase in the presence of a suitable phosphorous-vanadium mixed oxide catalyst.

BACKGROUND OF THE INVENTION

It is well known that in the reactor, alongside the conversion reaction of butane into maleic anhydride:

$$C_4H_{10} + 3.5\ O_2 \rightarrow C_4H_2O_3 + 4H_2O$$

other secondary reactions take place, among which the main ones are butane combustion reactions forming carbon monoxide and carbon dioxide:

$$C_4H_{10} + 4.5\ O_2 \rightarrow 4CO + 5H_2O$$

$$C_4H_{10} + 6.5\ O_2 \rightarrow 4CO_2 + 5H_2O$$

Carbon monoxide is normally produced in excess and the molar ratio between carbon dioxide and carbon monoxide typically ranges between 0.6 and 1.0.

Reactions are strongly exothermic and the heat of reaction is suitably removed by circulating a coolant (usually molten salts) in the reaction section which thereafter release heat to a steam generator.

Conversion, selectivity and reaction yield depend on reaction conditions, mainly on feed composition, pressure, temperature and space velocity (the latter measured as standard volume of gas fed per hour per catalyst volume unit).

By conversion it is meant the butane percentage in weight fed to the reactor, which is transformed into the product or by-products.

By selectivity it is meant the amount of maleic anhydride expressed as the percentage (w/w) of the butane converted.

The conversion product by selectivity determines yield, which identifies the amount of maleic anhydride produced, expressed as total butane percentage in weight fed to the reactor.

Non-converted butane is present in the reaction effluent.

The maleic anhydride produced is recovered by selective absorption of maleic anhydride from reaction gases by means of an absorption medium which may be water or a selective organic solvent for instance preferably chosen among diesters of phthalic acid such as dibutyl phthalate and dioctyl phthalate.

Conventionally, absorption is carried out at a pressure which is slightly higher than atmospheric pressure, and which is sufficient to ensure exhaust gas transfer to an incinerator where organic compounds (mostly butane) are burnt and, after heat recovery, are exhausted into the atmosphere.

The result is that non-converted butane jeopardizes the process both in terms of yield, therefore higher raw material costs, and in terms of a higher carbon dioxide release into the air.

In order to increase yield, a fraction of the exhaust gases may be taken into consideration for recycling into the reaction.

Recycling of exhaust gases—containing non-converted raw materials—is a well-known procedure which has been used in various industrial processes, including catalytic oxidations in the vapor phase.

For example, this procedure is normally used in the catalytic oxidation of ethylene to ethylene oxide.

In the field of maleic anhydride production from butane, reaction gas recycling is detailed in the article "Oxidation of Butane to Maleic Anhydride", by Bissot and Benson, found at pages 57–60 of Industrial Engineering Chemistry, Book 2, no. 1, March 1963.

However, the article describes recycling within a process including a number of reactors connected in series with maleic anhydride separation between them.

This process received no industrial interest because of its complexity and the high investments that it involved.

Recycling was also reported in a number of patents (such as U.S. Pat. No. 3,899,516, U.S. Pat. No. 3,904,652, U.S. Pat. No. 4,222,945, U.S. Pat. No. 4,342,699; U.S. Pat. No. 5,011,945). All of them featuring use of oxygen or enriched air as oxidizing medium.

All patents, patent applications, and publications referred to in the present specification are incorporated herein by reference in their entirety.

In all processes using oxygen, exhaust gas recycling to the reaction is an essential factor, it being anyhow necessary to dilute oxygen and prevent explosion hazards.

Moreover, these processes are characterized by the operating conditions which remarkably differ from processes wherein air is used.

A typical use is high butane charge concentrations, obtaining low conversions per pass, so as to limit formation of gaseous by-product such as carbon monoxide and carbon dioxide which should be removed by releasing a fraction of exhaust gases.

U.S. Pat. No. 4,231,943 discloses exhaust gas recycling combined with use of air as oxidizing medium incorporated herein by reference in its entirety. The process described in this latter patent is inspired by principles which are typical of processes based on use of oxygen, i.e. low butane conversions per pass, relatively high concentration of butane and low concentration of oxygen in the feed. Process chemistry shows that, even under optimum conditions, when using air, at least 4 tons of inert gas (nitrogen) should be released per each ton of maleic anhydride produced.

Considering the high inlet and outlet butane concentrations with regard to the reactor, this operation involves very high butane losses in the released gases.

In order to prevent this, U.S. Pat. No. 4,231,943 provides a unit for the removal of butane from the released gases by absorption on activated carbon.

Butane absorption by activated carbon—due to the large gas deliveries to be treated at low pressure—is complicated and requires very high and costly amounts of absorption medium.

U.S. Pat. No. 5,011,945 describes a total recycle process wherein the oxidizing medium is oxygen mixed with exhaust reaction gases, to a large extent consisting of carbon monoxide and carbon dioxide, in molar proportion of at least 1 to 1, where the butane oxidation catalyst is a catalyst of the phosphorus vanadium mixed oxide (V.P.O.) type with addition of a co-metal comprising molybdenum.

In the mentioned process the recycling gas contains a high concentration of carbon monoxide, presenting inherent risks of loss of control and of deflagration in the butane oxidation reactor.

U.S. Pat. No. 5,688,970 describes a process where the oxidizing medium is a mixture of air and a fraction of reaction exhaust gases, characterized by the fact that the recovery of maleic anhydride (and consequently the recycle of exhaust gases) is carried out under pressure.

Compared to the conventional technology, the above mentioned process, makes it possible to get an improved selectivity and a higher yield (and consequently a lower butane consumption), a lower power consumption, and also a reduction in the carbon dioxide release to the atmosphere.

Although in principle the process described in said U.S. Pat. No. 5,688,970 might be applied to use enriched air or oxygen as oxidizing medium, the potential advantages of the use of oxygen is limited by the fact that an increase of the percentage of exhaust gases being recycled, consequent to the use of oxygen, increases the concentration of carbon monoxide in the feed to the reactor, with enhanced risk of deflagration.

US Pat. No. 5,126,463 describes a process where the oxidizing medium is pure oxygen mixed into exhaust gases of reaction, characterized by the fact that the carbon monoxide produced in the reaction is converted into carbon dioxide reacting over an oxidation catalyst (copper oxide-manganese oxide). The advantages of such process appear to be limited by the fact that the exhaust gases of reaction contain a high concentration of carbon dioxide, specified to be not less than 60% by volume, preferably about 80% by volume, which may adversely influence the activity and lifetime of conventional V.P.O. catalysts.

Furthermore, since the concentration of carbon monoxide in the recycling gases is low, a large volume of recycling gases, shown to be about 18 ton of gas per ton of maleic anhydride produced in Table II of U.S. Pat. No. 5,126,463, is to be processed in the catalytic converter of carbon monoxide.

The above mentioned features may have a significant impact on the performances and economics of the process described in the abovementioned patent.

DESCRIPTION OF THE INVENTION

Therefore, a first and foremost aim of the present invention is that of providing a process for an efficient and safe production of maleic anhydride wherein the above mentioned problems and troubles are substantially overcome in an industrially feasible manner.

According to the present invention, the above aim has been accomplished by providing a process for the production of maleic anhydride by the oxidation in vapor phase of n-butane, wherein the oxidizing medium is pure oxygen (or enriched air) mixed in recycled reaction gases, reacting over a suitable phosphorus vanadium mixed oxide (V.P.O.) catalyst, with or without modifying components, to afford maleic anhydride with a high yield and a high productivity, characterized by the fact that the concentration of the by product carbon oxides in the maleic anhydride reactor feed will be controlled in way to maintain a carbon dioxide to carbon monoxide molar ratio, optimized to allow the production of maleic anhydride with high yield and high productivity associated with a high degree of safety in operation.

The V.P.O. catalyst used in the instant process is preferably, but not limited to, a catalyst characterized by the fact that the precursor, prior to calcination, is pretreated by contact with an aliphatic anhydride, preferably acetic anhydride, and by the fact that the temperature rise during calcination is inferior to 1° C. per minute.

The process of the instant invention, is characterized by the following operations:

a) Preparing the reaction mixture consisting of oxygen, butane, carbon dioxide and a recycle gaseous stream being adjusted in such a way that the oxygen concentration in the reaction mixture ranges between 5% and 16% by volume, the butane concentration in the reaction mixture ranges between 2% and 20% by volume, the carbon dioxide concentration in the reaction mixture does not exceed 60% by volume and is in a molar ratio to carbon monoxide of at least 1.5 to 1.0, e.g. 1.5–10:1.

b) Feeding the reaction mixture to an oxidation reactor operating at inlet pressure between 2.03 to 6.03 bar where a suitable V.P.O. type catalyst causes butane to react at moderate conversion per pass rate, producing maleic anhydride with high selectivity and high productivity.

c) Cooling the reaction gases comprising oxygen, non converted butane, organic by products, carbon dioxide, carbon monoxide, water steam, inerts and maleic anhydride produced.

d) Recovering maleic anhydride by absorption into a solvent, preferably a selective organic solvent, operating the absorption at an outlet pressure ranging from 1.21 to 4.5 bar.

e) Water scrubbing the recycling exhaust gases after removal of maleic anhydride, so as to eliminate all organics present, except butane.

f) Compressing the recycling exhaust gases after the water scrubbing to the pressure of reaction.

g) Purging a fraction of the compressed exhaust gas in order to avoid accumulation of inerts (as nitrogen, argon) and of carbon oxides.

h) Washing said purge of the recycling exhaust gases with the selective organic solvent referred at point d) above in order to remove by absorption a large fraction of the butane contained in said purge gas stream. The absorbed butane is following desorbed in the maleic anhydride absorber and recovered in the recycling exhaust gases after the removal of maleic anhydride.

i) Adding fresh butane, a carbon dioxide rich stream and oxygen (or enriched air) to the compressed recycling stream of exhaust gases to form the reaction mixture having the characteristics described in step a) above.

j) Using as carbon dioxide rich stream either one of the following sources of carbon dioxide:
   1) Carbon dioxide produced by selective absorption and desorption from the gaseous purge of the recycling exhaust gases.
   2) Carbon dioxide rich stream produced by selective separation by membranes from a gaseous purge of the recycling exhaust gases.
   3) Carbon dioxide rich stream produced by selective oxidation of carbon monoxide to carbon dioxide of the gaseous purge from the recycling exhaust gases.
   4) Carbon dioxide from an external source.
   5) Carbon dioxide produced from a combination of the abovementioned sources.

The improvement in the performances of the process object of the present invention is due to the following major factors:

a) The concentration of butane, oxygen, carbon monoxide, carbon dioxide in the feed to the reactor is controlled in such a way as to assure a high selectivity and high productivity at the operating conditions of pressure and temperature of the reaction, over the V.P.O. catalyst used in the present process.

b) The relatively high concentration of carbon dioxide and the relatively high molar ration between carbon dioxide and carbon monoxide in the feed to the reactor, are beneficial towards lowering any possible risk of explosion and improving the transfer of heat in the reactor.

c) The non converted butane in the exhaust gases is recycled and is recovered to the reaction. The relatively high butane concentration makes it possible to operate the reaction with a relatively low conversion per pass rate and, consequently, with a higher selectivity.

d) The amount of butane lost in the purge gas is minimized by special absorption and desorption technique.

e) A relatively small volume of gas, the purge of the process, is to be processed in one auxiliary unit (either a carbon dioxide selective absorption and desorption unit, or a membrane separation unit, or a catalytic converter of carbon monoxide).

The amount of purge gas to be processed in the auxiliary unit, typically about 1 ton of gas per ton of maleic anhydride produced, is by far inferior to the amount of gas to be processed in the auxiliary units in other processes.

f) By using a suitable catalyst optimized to work under recycling conditions, it was found that the process object of the present invention leads to a safe operation, a better control on temperature peaks during reaction, a better heat transfer, a better selectivity and consequently a higher yield and higher productivity.

Summarizing, compared with the traditional technology or with the gas recycle technology, like for instance the technology described in U.S. Pat. No. 5,688,970, the process object of the present invention has the following advantages:

a) Best selectivity and yield (consequently a lower butane consumption)

b) Higher productivity (consequently higher production capacity in identical reactor)

c) Safe operation d) Improved environmental friendly feature, with a remarkable reduction in the carbon dioxide released into the environment, compared with other technologies in use.

DESCRIPTION OF PREFERRED EMBODIMENTS

The process of this invention is shown in the attached drawings wherein.

Figure 1:
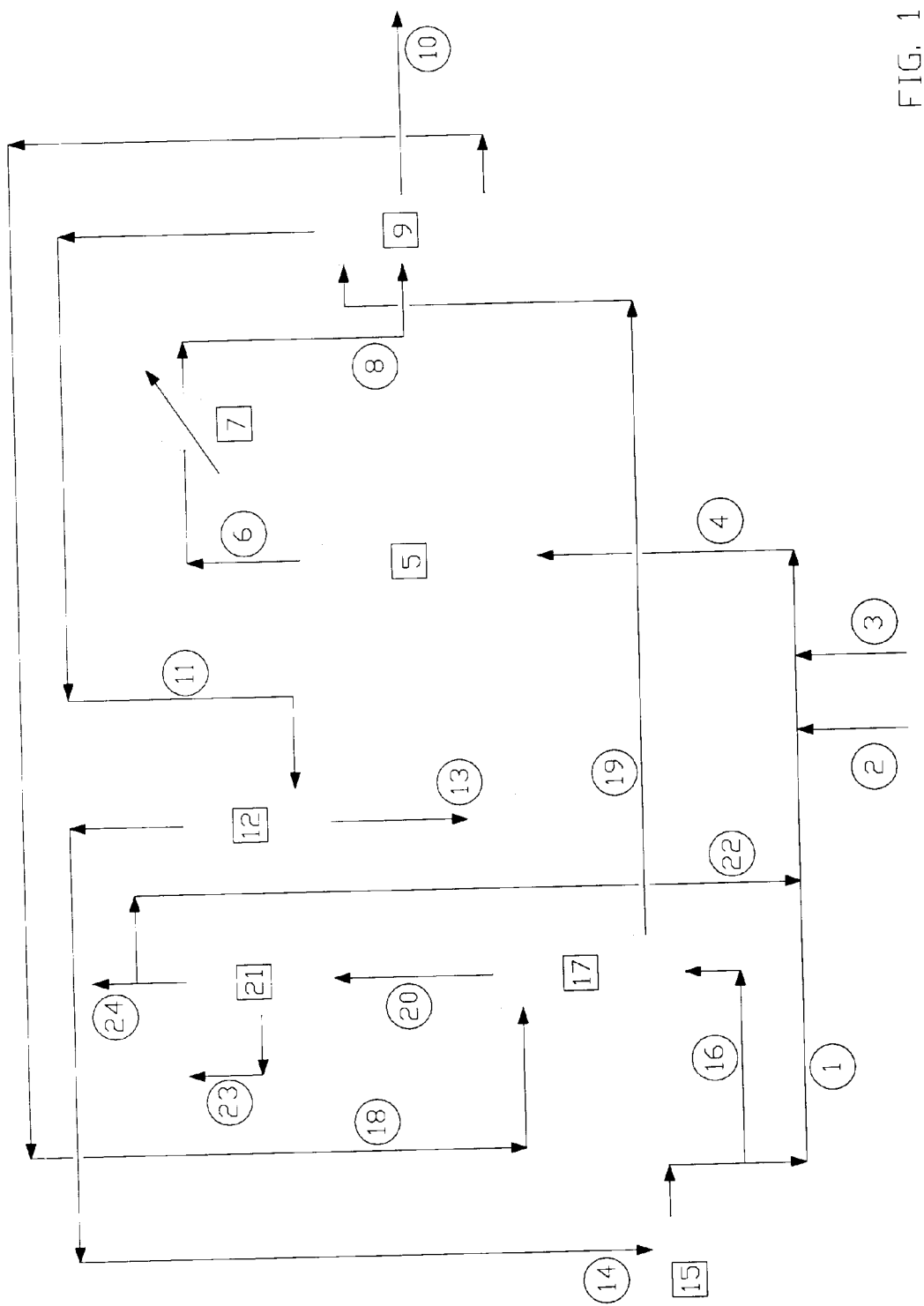
FIG. 1 shows a total recycle process using as co-feedstock carbon dioxide produced by selective absorption of carbon dioxide from a gaseous stream purged from the recycling exhaust gases of reaction.

With reference to FIG. 1, compressed exhaust gases in line I blend with the butane feed from line 2, with oxygen from line 3 and carbon dioxide from line 22, at a pressure ranging between 2.03 and 6.03 bar.

The mixture thus obtained passes through line 4 and is fed to the reactor 5, which is preferably of the longitudinal flow fixed bed type, even though the features of the present invention make it applicable to other types of reactors, for example fluidized bed reactors.

By means of a suitable V.P.O. catalyst, especially designed to operate in gas recycling conditions, butane is oxidized to maleic anhydride and by products in the reactor.

A suitable V.P.O. catalyst is, but not limited to, a catalyst prepared according the following steps:

a) contacting a phosphorus compound and a vanadium compound in an organic solvent under conditions which will provide a catalyst precursor having a phosphorus to vanadium atom ratio between about 0.9 to 1.4, and having more than 90 atom percent of the vanadium in the tetravalent state;

b) recovering the precursor;

c) drying the precursor, limiting the maximum temperature, in an oxygen containing atmosphere, to a value which will not substantially oxidize the residual organic materials arising from the organic solvent used;

d) submitting the precursor, prior to calcination, to a treatment by contacting with a stream of dry inert gas containing vapors of an aliphatic anhydride, having from 4 to 8 carbon atoms, preferably acetic anhydride, at a temperature not to exceed about 200° C.

e) providing an atmosphere selected from the group consisting of air, steam, inert gases and mixture thereof, and calcining the precursor in said atmosphere, by raising the temperature, as measured in the precursor, above 200° C. at less than 1° C. per minute to a temperature greater than 350° C., but no greater than 550° C. and maintaining the temperature for a time effective in giving a vanadium oxidation state not greater than +4.5 and in completing the conversion to generate an active catalyst.

Effluent gases from the reactor 5 comprises non-converted butane, maleic anhydride, carbon monoxide, carbon dioxide, steam, by-product organic compounds such as acetic acid and acrylic acid, and inerts (such as nitrogen and argon) present in the oxygen feed. Effluent gases pass through the reactor effluent line 6, are cooled in unit 7 and conveyed through line 8 to an absorber stripper unit 9 where the maleic anhydride product is recovered and discharged through line 10. The absorber-stripper unit 9 preferably uses an organic solvent as absorbing medium, or even better, a solvent as described in U.S. Pat. No. 5,069,687, incorporated herein by reference in its entirety.

The recycling gases from line 11 are fed to a water-scrubber column 12 where water-soluble organic compounds are separated in the form of condensate which passes through line 13.

Since butane is insoluble in the recycle gas, it is retained by the gas after scrubbing. The recycling gases after scrubbing are fed via line 14 to a compressor 15.

The largest fraction of gases leaving the compressor pass through line 1 and are recycled to the reactor 5, while a small fraction pass through line 16 and are purged out.

The purge gas from line 16 is fed to an absorber 17 where the gas is washed with a stream of lean organic solvent from line 18. The lean organic solvent being fed to the absorber 17 from the maleic anhydride absorber stripper unit 9 through line 18.

A large fraction of the butane present in the purge gas is recovered by absorption in the solvent in the absorber 17.

The solvent leaving the absorber 17 flows via line 19 to the maleic anhydride absorber 9 where butane is desorbed and recovered into the recycling gases of line 11.

The purge gas leaving the butane absorber 17 via line 20 is fed to a conventional carbon dioxide recovery unit 21, preferably of the absorption type, where the carbon dioxide is separated. A fraction of carbon dioxide passes through line 22 and is recycled to the reaction loop to adjust its concentration in the recycling gases.

In this way the molar concentration of carbon dioxide in the recycling gases is at least 1.5 times higher than the molar concentration of carbon monoxide.

The excess of the recovered carbon dioxide of line 24 may be used as inert gas or for other industrial uses.

The purge gas leaving the carbon dioxide recovery unit via line 23 may be conveyed to an incinerator.

The advantages offered by this invention are evidenced by Example A hereinafter.

In order to make the comparison easier, Example A refers to a plant that has an identical capacity as the plant of Example 1 and Example 2 given in U.S. Pat. No. 5,688,970, which means 3100 Kg/hr maleic anhydride produced.

Compared with the partial recycle process using air as oxidant, described in U.S. Pat. No. 5,688,970 (CASE A), the process object of the present invention (CASE B) presents the following global rates listed in TABLE 1:

TABLE 1

|  | CASE A | CASE B |
| --- | --- | --- |
| Total yield (Kg of maleic anhydride per Kg of butane) | 1.03 | 1.18 |
| Productivity (Kg/hr of maleic anhydride per Mc of catalyst) | 78 | 130 |

Figure 2:
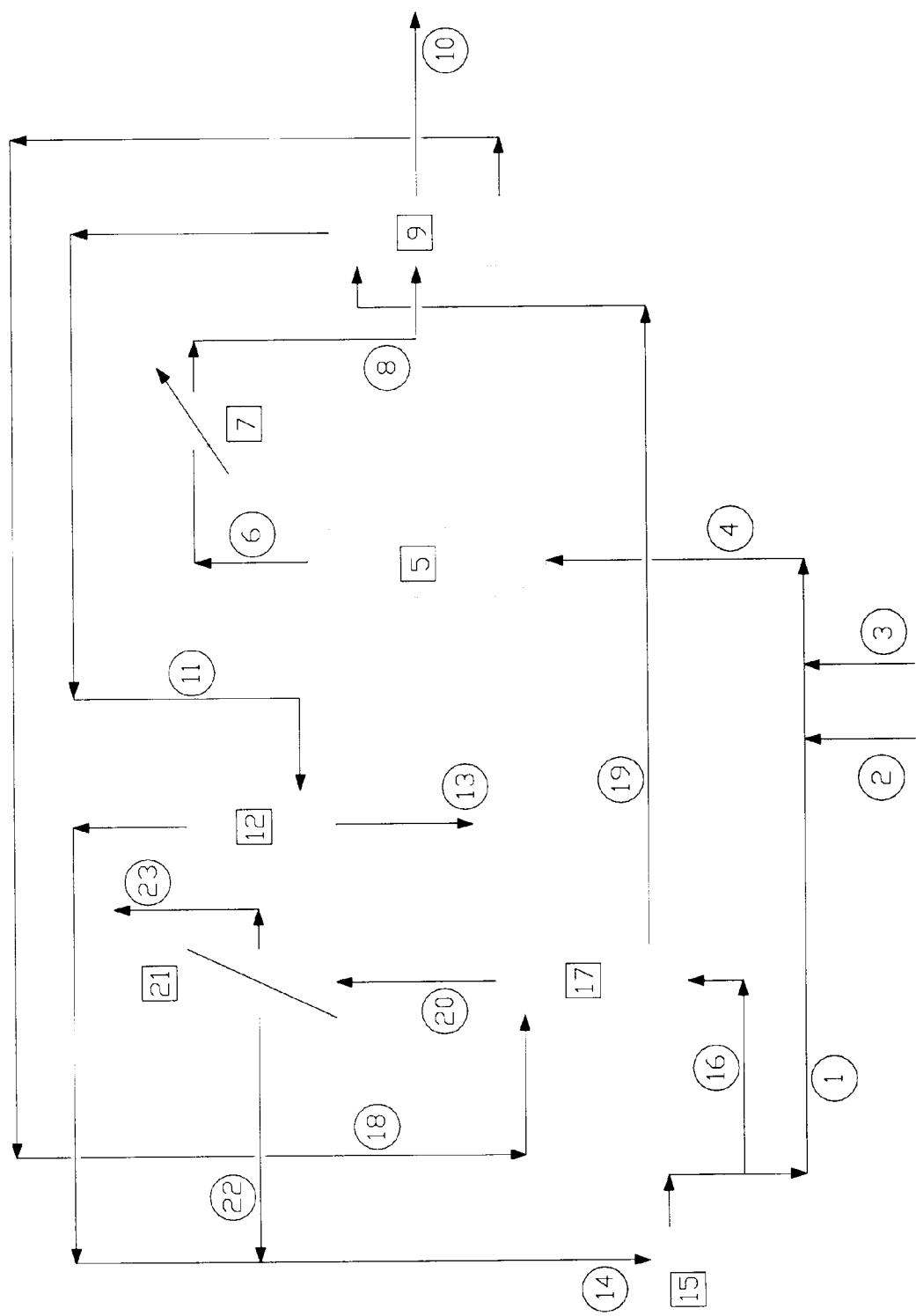
FIG. 2 shows a total recycle process using as co-feedstock a carbon dioxide rich stream produced by selective separation by membranes from a gaseous stream purged from the recycling exhaust gases of reaction.

In the process shown in FIG. 2 the purge gas leaving the butane absorber 17 via line 20 is fed to a membrane unit 21 which separates selectively as permeate a carbon dioxide rich stream of line 22 which is recycled to the process, while the reitentate stream of line 23 is purged to an incinerator.

Figure 3:
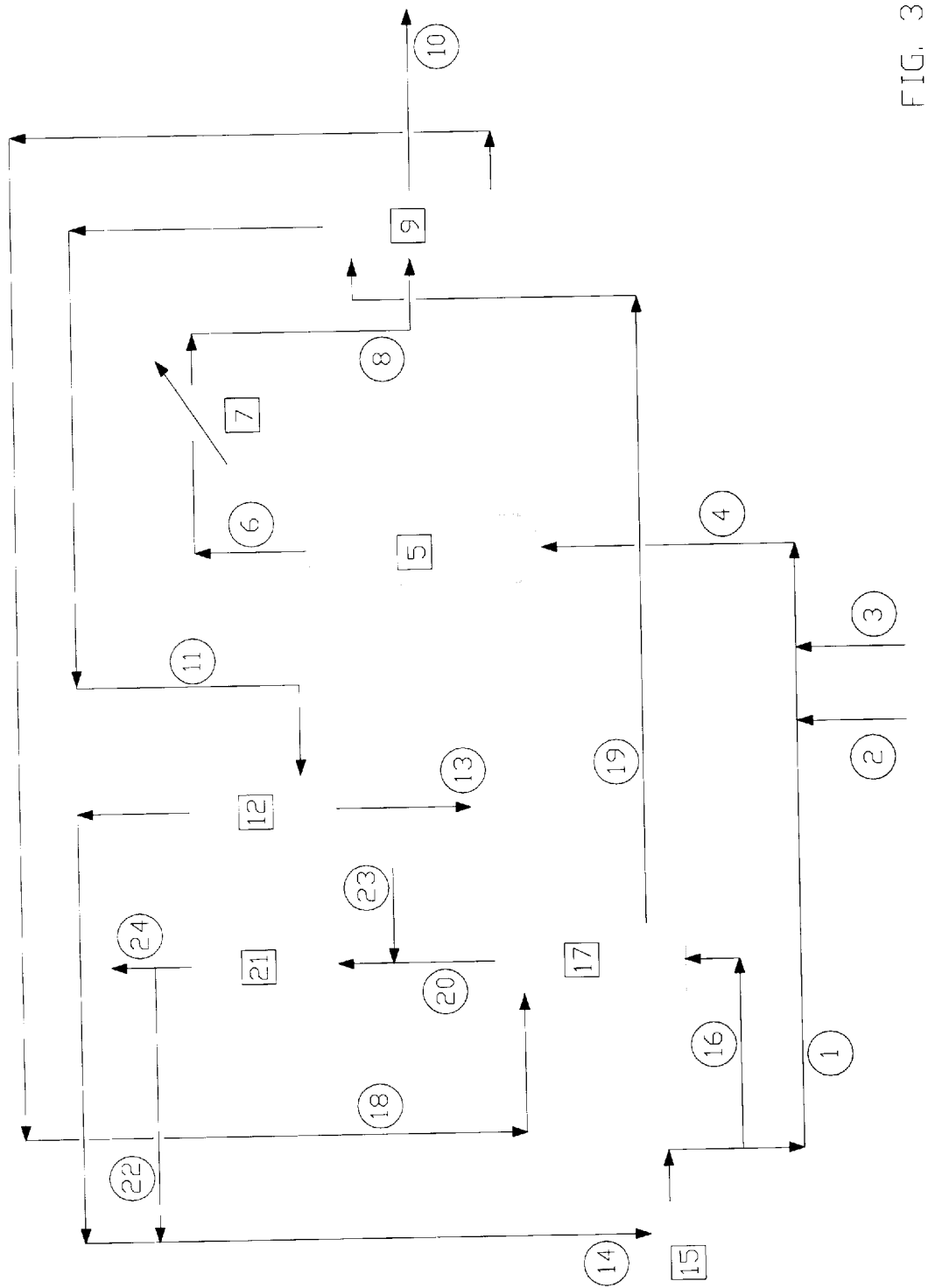
FIG. 3 shows a total recycle process using as co-feedstock carbon dioxide produced by selective catalytic oxidation of carbon monoxide to carbon dioxide from a gaseous stream purged from the recycling exhaust gases of reaction.

The process shown in FIG. 3 differs for a different treatment of the purge gas stream.

Here the purge gas leaving the butane absorber via line 20 with added oxygen line 23 is fed to a catalytic converter 21 designed to oxidize selectively carbon monoxide into carbon dioxide.

A stream of oxygen from line 23 is added to the purge gas as necessary to complete the selective oxidation of carbon monoxide.

The catalytic converter 21 will be preferably of the tubular type, with a cooling medium in the shell to control the temperature rise due to the exothermic heat of oxidation.

A fraction of the converter effluent via line 24 will be conveyed to an incinerator, while the remaining fraction, rich in carbon dioxide, will be recycled to the process via line 22.

Figure 4:
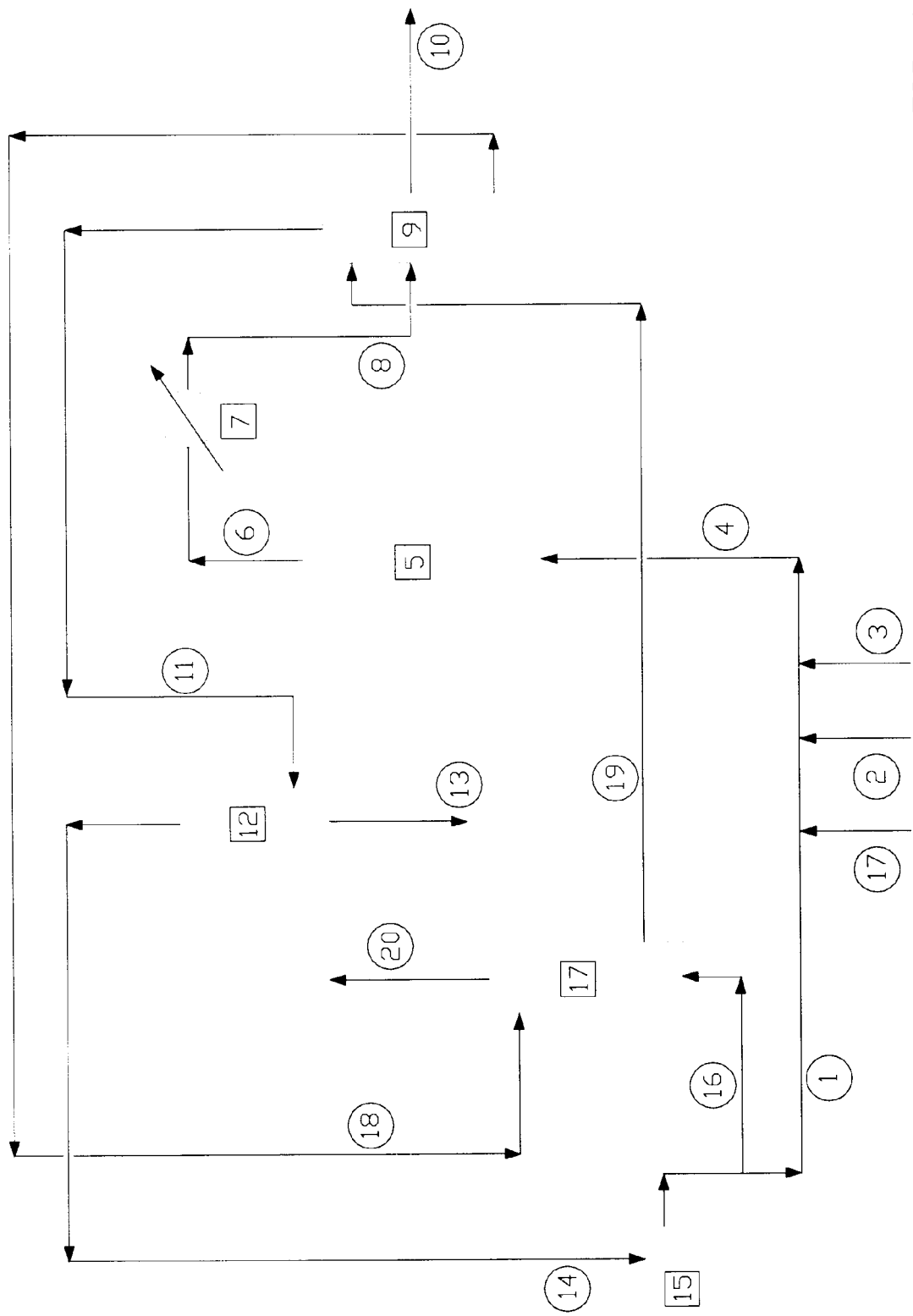
FIG. 4 shows a total recycle process using as co-feedstock carbon dioxide from an external source.

The process shown in FIG. 4 differs from the processes shown in FIG. 1, FIG. 2 and FIG. 3 for the fact that it uses as feed a carbon dioxide rich stream from an external source.

No treatment is provided for the purge gas except the washing with lean organic solvent as previously described.

The purge gas leaving the butane absorber 17 via line 20 is conveyed to an incinerator.

The compressed exhaust gases pass through line 1 and blend with the butane feed from line 2, oxygen from line 3 and carbon dioxide from an external source from line 17 to form the mixture of line 4 feeding the maleic anhydride reactor 5.

EXAMPLE A

With reference to FIG. 1 annexed hereto, the process object of this invention typically runs as follows:

75356 Kg/hr of recycle gases(from line 1 at 4.5 bar are mixed with 1300 Kg/hr of carbon dioxide from line 22, 5832 Kg/hr of pure oxygen from line 2 and 2630 Kg/hr of butane from line 3.

The total mixture in line 4 makes up the feed to the reactor 5.

The feed is 85118 Kg/hr and consists of the composition shown in TABLE 2:

TABLE 2

| Oxygen | 12.3% by volume |
| --- | --- |
| Water steam | 3.0% by volume |
| Butane | 5.6% by volume |
| Carbon monoxide | 24.0% by volume |
| Carbon dioxide | 55.1% by volume |
| Inerts | traces |

The oxidation reactions take place in the longitudinal flow reactor 5.

The composition of the gases exiting the reactor 5 through line 6 (typical values) is as shown in TABLE 3:

TABLE 3

| Oxygen | 4.1% by volume |
| --- | --- |
| Water steam | 11.3% by volume |
| Butane | 3.6% by volume |
| Carbon monoxide | 24.6% by volume |
| Carbon dioxide | 55.0% by volume |
| Maleic anhydride | 1.4% by volume |
| Organic by-products | traces |
| Inerts | traces |

After cooling in unit 7 the reactor effluent stream 8 is fed to a maleic anhydride recovery unit 9 where maleic anhydride is absorbed by a selective organic solvent (preferably dibutylphthalate) from line 19 containing about 144 Kg/hr of butane absorbed from the purge gas. The maleic anhydride, recovered from the solvent, passing through line 10 amounts to 3100 Kg/hr.

In the maleic anhydride absorber stripper unit 9 the butane contained in the solvent is stripped and recovered in the gases leaving the absorber 9.

The gases leaving the absorber 9, at a rate of 82162 Kg/hr, are conveyed via line 11 to a water scrubbing column 12 where water and organic compounds are condensed to discharge through line 13. The gases leaving the water scrubbing column 12, at a rate of 78767 Kg/hr, recycle via line 14 to the suction of the compressor 15.

A relatively small fraction of the compressed gases, 3411 Kg/hr, is conveyed via line 16 to a butane absorber 17, where the fraction is washed with a stream of lean solvent from line 18 being fed to the butane absorber 17 from the maleic anhydride absorber stripper unit 9.

About 144 Kg/hr of butane present in the purge gas is recovered in the solvent and is passed through line 19. The gaseous effluent from the butane absorber 17, at a rate of 3291 Kg/hr, flows through line 20 to a carbon dioxide recovery unit 21.

The carbon dioxide recovery unit 21 separates 2236 Kg/hr of carbon dioxide, of which 1300 Kg/hr are returned via line 22 to the reactor feed while the remaining 936 Kg/hr may be recovered from line 24 for use as inert gas or for other uses.

The purge gas leaving the carbon dioxide recovery unit, 1055 Kg/hr, is conveyed to an incinerator (not shown) via line 23.

Totally the following rates shown in TABLE 4 are obtained.

TABLE 4

| Maleic anhydride produced | 3100 Kg/hr |
|---|---|
| Butane feed | 2630 Kg/hr |
| Oxygen feed | 5832 Kg/hr |
| Yield | 1.18 Kg/Kg |
| Gas conveyed to incinerator | 1055 Kg/hr |

Examples 1 and 2 of U.S. Pat. No. 5,688,970 show the following rates listed in TABLE 5.

TABLE 5

|  | EXAMPLE 1 | EXAMPLE 2 |
|---|---|---|
| Maleic anhydride produced | 3100 Kg/hr | 3100 Kg/hr |
| Butane feed | 3008 Kg/hr | 3289 Kg/hr |
| Oxygen feed | — | — |
| Yield | 1.03 Kg/Kg | 0.94 Kg/Kg |
| Gas conveyed to incinerator | 33364 kg/hr | 75057 Kg/hr |

Comparing the performances, the advantages of the process of this invention are evident.

In particular the following is obtained:

a) Reduced consumption of butane, from 122 to 212 kg per ton of maleic anhydride produced.

b) Safer operating conditions due to the antideflagration influence of the relatively high concentration of carbon dioxide in the gas mixture.

c) Very remarkable reduction in gas conveyed to incineration

Furthermore the process of this invention offers a substantially higher productivity allowing an important reduction of the dimensions of the maleic anhydride reactor, with substantial savings on investment.

The performances and rates do not differ significantly in case the process is operated according the embodiments of FIG. 2, FIG. 3 or of FIG. 4.

It is understood that the invention is not limited to the above embodiments and that many changes may be made without departing from the spirit of the invention.

We claim:

1. A process for the production of maleic anhydride by the oxidation of n-butane with molecular oxygen or a molecular oxygen containing gas in the vapor phase at a temperature of about 300° C. to 550° C. in the presence of a suitable phosphorous-vanadium mixed oxide catalyst, with or without modifying components, comprising the steps of:

a) Preparing a reaction mixture comprising oxygen, butane, carbon dioxide and a recycle gaseous stream, wherein the oxygen concentration in the reaction mixture ranges from 5 to 16% by volume, the butane concentration in the reaction mixture ranges from 2 to 20% by volume, the carbon dioxide concentration in the reaction mixture does not exceed 60% by volume and is in a molar ratio to carbon monoxide of at least 1.5 to 1.0, b) Feeding the reaction mixture to an inlet of an oxidation reactor operating at an inlet pressure in the range of 2.03 to 6.03 bar where a suitable V.P.O. catalyst causes a portion of the butane to react to produce maleic anhydride, c) Cooling the reaction gases comprising oxygen, non-converted butane, organic by-products, carbon dioxide, carbon monoxide, water steam and maleic anhydride produced, d) Recovering the maleic anhydride by absorption in a solvent in a maleic anhydride absorber, operating the absorption at an outlet pressure ranging from 1.21 to 4.5 bar, to form a stream comprising recovered maleic anhydride and a stream comprising recycling exhaust gases, e) Water scrubbing the recycling exhaust gases after removal of maleic anhydride, so as to eliminate all organics present, except butane, f) Compressing the recycling exhaust gases after the water scrubbing to the pressure of reaction, g) Separating the compressed recycling exhaust gases to form a first fraction and a second fraction, purging said first fraction of the compressed recycling exhaust gases to avoid accumulation of inerts and of carbon oxides, said recycle gaseous stream comprising said second fraction, and optionally h) Washing said purge of the compressed recycling exhaust gases with the solvent referred to at step d), to remove by absorption a large fraction of the butane contained in said purge gas stream, the absorbed butane being then desorbed in the maleic anhydride absorber and recovered in the recycling exhaust gases after the removal of maleic anhydride in the maleic anhydride absorber.

2. A process according to claim 1, comprising:

h) washing said purge of the compressed recycling exhaust gases with the solvent referred to at step d), to remove by absorption a large fraction of the butane contained in said purge gas stream, the absorbed butane being then desorbed in the maleic anhydride absorber and recovered in the recycling exhaust gases after the removal of maleic anhydride in the maleic anhydride absorber.

3. A process according to claim 1, comprising:

i) Adding fresh butane, a carbon dioxide rich stream and a member of the group consisting of oxygen and enriched air to the recycle gaseous stream to form the reaction mixture having the characteristics described in step (a) above.

4. A process according to claim 1, wherein the carbon dioxide is provided from a source selected from the group consisting of:

I) Carbon dioxide produced by selective absorption and desorption from the gaseous stream purged from the recycling exhaust gases, II) Carbon dioxide rich stream produced by selective separation by membranes from a gaseous purge of the recycling exhaust gases, III) Carbon dioxide rich stream produced by selective oxidation to carbon dioxide of carbon monoxide contained in the gaseous stream purged from the recycling exhaust gases, IV) Carbon dioxide from an external source, and V) Carbon dioxide produced from a combination of the abovementioned sources.

5. A process according to claim 1, wherein said oxidation reactor is selected from the group consisting of a fixed bed reactor and a fluidized bed reactor.

6. A process according to claim 1, wherein the catalytic reactions in said reactor are carried out at a reaction temperature of 370–449° C.

7. A process according to claim 6, wherein said reaction temperature is 400° C.

8. A process according to claim 1, wherein said oxidation reactor inlet pressure is from 3.0 to 4.5 bar.

9. A process according to claim 1, wherein the oxygen content in the gases feeding the reactor is from 8 to 14% by volume.

10. A process according to claim 1, wherein the carbon dioxide to carbon monoxide molar ratio in the gases feeding the reactor is from 1.5 to 10.0.

11. A process according to claim 1, wherein the butane content in the gases feeding the reactor is from 3 to 8% by volume.

12. A process according to claim 1, wherein said catalytic reaction is carried out a space velocity from 1000 to 4000 $hr^{-1}$.

13. A process according to claim 12, wherein said space velocity is from 2000 to 3000 $hr^{-1}$.

14. A process according to claim 1, wherein a volatile phosphorus compound is added to the reaction feed mixture to control the activity of the catalyst.

15. A process according to claim 14, wherein the content of phosphorus in the reaction feed is between 1 and 20 ppm by volume.

16. A process according to claim 1, wherein the catalyst comprises a phosphorus-vanadium mixed oxide, with or without modifying components.

17. A process according to claim 1, wherein the solvent referred at steps d) and h) is selected from diesters of phthalic acid.

18. A process according to claim 17, wherein said diesters of phthalic acid are selected from the group consisting of dibutylphthalate and dioctylphthalate.

19. A process according to claim 1, wherein the carbon dioxide is provided from a carbon dioxide rich stream recovered from the gaseous stream purged from the recycling exhaust gases by selective absorption and desorption in a carbon dioxide recovery unit.

20. A process according to claim 19, wherein the carbon dioxide recovery unit is a sodium carbonate, potassium carbonate, amine, SULFINOL, RECTISOL, or PURISOL process.

21. A process according to claim 1, wherein the carbon dioxide is provided from a carbon dioxide rich stream produced by selective oxidation to carbon dioxide of the carbon monoxide contained in a purge stream of the recycling gases in a selective oxidation unit.

22. A process according to claim 21, wherein the selective oxidation unit uses a catalyst capable of selectively oxidizing carbon monoxide to carbon dioxide in a gas having an oxygen to carbon monoxide molar ratio from 0.5 to 3.0.

23. A process according to claim 22, wherein the carbon monoxide oxidation catalyst comprises a supported precious metal catalyst.

24. A process according to claim 22, wherein the carbon monoxide oxidation catalyst comprises a supported precious metal catalyst selected from at least one member of the group consisting of platinum, rhodium, ruthenium, and palladium.

25. A process according to claim 1, wherein the absorption of butane from the purge gas of step h) is provided after said carbon dioxide is produced by at least one step selected from the group consisting of:

selective absorption and desorption of carbon dioxide from the gaseous stream purged from the recycling exhaust gases to produce said carbon dioxide, selective oxidation to carbon dioxide of carbon monoxide contained in the gaseous stream purged from the recycling exhaust gases, or selective separation by membranes from a gaseous purge of the recycling exhaust gases.

26. A process according to claim 1, wherein a carbon dioxide rich stream is recovered by selective separation by membranes from the gaseous purge of the recycling exhaust gases.

27. A process according to claim 1, wherein water is used as solvent for the recovery of maleic anhydride and/or wherein the sequence of operations does not include the absorption of butane from the purge gas mentioned at step h).

28. A process according to claim 1, wherein the inerts comprise nitrogen and argon.

29. A process according to claim 1, wherein in said reactor the V.P.O. catalyst causes the butane to react at moderate conversion per pass producing maleic anhydride to produce maleic anhydride with high selectivity and high productivity.

30. A process according to claim 1, wherein said solvent in which the maleic anhydride is recovered comprises a selective organic solvent.

31. A process according to claim 1, wherein in said step a) said reaction mixture comprises pure oxygen, butane, carbon dioxide and said recycle gaseous stream.

32. A process according to claim 1, wherein a volatile organophosphorus compound is added to the reaction feed mixture to control the activity of the catalyst.

* * * * *